United States Patent
Kim et al.

(10) Patent No.: US 10,607,340 B2
(45) Date of Patent: Mar. 31, 2020

(54) REMOTE IMAGE TRANSMISSION SYSTEM, DISPLAY APPARATUS, AND GUIDE DISPLAYING METHOD THEREOF

(71) Applicant: SAMSUNG ELECTRONICS CO., LTD., Suwon-si (KR)

(72) Inventors: Min-soeng Kim, Seoul (KR); Joo-yoo Kim, Seoul (KR); Yong Kim, Seoul (KR); Soo-wan Kim, Yongin-si (KR); Eung-sun Kim, Seoul (KR); Jae-geol Cho, Yongin-si (KR); Tae-hwa Hong, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 80 days.

(21) Appl. No.: 15/403,309

(22) Filed: Jan. 11, 2017

(65) Prior Publication Data
US 2017/0236273 A1 Aug. 17, 2017

(30) Foreign Application Priority Data
Feb. 17, 2016 (KR) .................. 10-2016-0018533

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0002* (2013.01); *A61B 5/0013* (2013.01);
(Continued)

(58) Field of Classification Search
CPC .................. A61B 5/0013; A61B 1/00; A61B 2017/00203; A61B 2576/00; A61B 34/30;
(Continued)

(56) References Cited

U.S. PATENT DOCUMENTS

| | | | | |
|---|---|---|---|---|
| 6,018,587 A * | 1/2000 | Cabib | .................. | G01J 3/12 382/165 |
| 6,837,432 B2 * | 1/2005 | Tsikos | ................... | G02B 26/10 235/462.01 |
| 7,889,931 B2 * | 2/2011 | Webb | ................ | G01N 21/8806 382/141 |
| 8,488,246 B2 * | 7/2013 | Border | ............... | G02B 27/017 353/28 |
| 8,655,053 B1 * | 2/2014 | Hansen | ................. | G06Q 10/10 382/154 |
| 8,908,928 B1 * | 12/2014 | Hansen | ............. | G06K 9/00362 382/111 |

(Continued)

FOREIGN PATENT DOCUMENTS

| | | |
|---|---|---|
| JP | 10-285587 A | 10/1998 |
| JP | 2000-224612 A | 8/2000 |

(Continued)

OTHER PUBLICATIONS

International Search Report (PCT/ISA/210) dated Apr. 17, 2017 by the International Searching Authority in counterpart International Patent Application No. PCT/KR2017/000751.
(Continued)

*Primary Examiner* — Aklilu K Woldemariam
(74) *Attorney, Agent, or Firm* — Sughrue Mion, PLLC

(57) ABSTRACT

A remote image transmission system, a display apparatus, and a guide displaying method of a display apparatus are provided. The remote image transmission system includes: an image capturing apparatus including a plurality of image pickup devices that are spaced from each other, the image capturing apparatus being configured to transmit, to a display apparatus, a plurality of images which are captured by the plurality of image pickup devices; and a display apparatus configured to generate a guide object indicating physical information of a captured object by using the plurality of received images, and to display the generated guide object and at least one of the plurality of images.

18 Claims, 27 Drawing Sheets

(51) Int. Cl.

| | | |
|---|---|---|
| G06K 9/32 | (2006.01) | |
| A61B 5/107 | (2006.01) | |
| H04N 5/232 | (2006.01) | |
| H04N 5/225 | (2006.01) | |
| G16H 30/20 | (2018.01) | |
| G16H 40/67 | (2018.01) | |
| G06K 9/52 | (2006.01) | |
| G06K 9/62 | (2006.01) | |
| G06T 7/60 | (2017.01) | |
| G06T 17/00 | (2006.01) | |
| H04N 5/247 | (2006.01) | |
| H04N 5/33 | (2006.01) | |
| H04N 5/235 | (2006.01) | |
| H04N 13/239 | (2018.01) | |

(52) U.S. Cl.
CPC .......... *A61B 5/0022* (2013.01); *A61B 5/0064* (2013.01); *A61B 5/0077* (2013.01); *A61B 5/1072* (2013.01); *A61B 5/1079* (2013.01); *A61B 5/444* (2013.01); *A61B 5/445* (2013.01); *A61B 5/4836* (2013.01); *A61B 5/742* (2013.01); *G06K 9/3241* (2013.01); *G06K 9/52* (2013.01); *G06K 9/6201* (2013.01); *G06T 7/60* (2013.01); *G06T 17/00* (2013.01); *G16H 30/20* (2018.01); *G16H 40/67* (2018.01); *H04N 5/2258* (2013.01); *H04N 5/23206* (2013.01); *H04N 5/23222* (2013.01); *H04N 5/23293* (2013.01); *H04N 5/247* (2013.01); *H04N 5/33* (2013.01); *G06K 2209/21* (2013.01); *G06T 2207/30088* (2013.01); *H04N 5/2256* (2013.01); *H04N 5/2354* (2013.01); *H04N 5/23245* (2013.01); *H04N 13/239* (2018.05)

(58) Field of Classification Search
CPC ....... A61B 5/00; A61B 5/0002; A61B 5/1032; A61B 5/445; A61B 90/36; A61B 90/361; A61B 5/441; A61B 5/0077; A61B 5/742; A61B 2576/02; A61B 5/004; A61B 5/442; A61B 5/7475; A61B 5/0022; A61B 5/0064; A61B 5/1072; A61B 5/1079; A61B 5/444; A61B 1/00096; A61B 1/041; A61B 1/273; A61B 5/1076; A61B 5/411; A61B 5/44; A61B 5/02416; A61B 5/02427; A61B 5/02433; A61B 5/02438; A61B 5/1123; A61B 5/4812; A61B 5/681; G06F 19/00; G06F 19/321; G06F 19/3418; G06F 17/30247; G06F 17/3028; G06F 1/1626; G06F 1/163; G06F 1/1684; G06F 3/00; G06F 19/34; G06F 2203/04105; G06F 3/0488; G06F 3/14; G01N 2021/95615; G01S 19/41; G01S 19/43; G01S 17/023; G01S 17/10; G01S 19/09; G01S 19/25; G01S 19/35; G01S 19/48; G01S 19/51; G01S 5/00; G01S 7/4812; G01S 7/4813; G06K 9/00483; G06K 9/52; G06T 2207/10024; G06T 2207/20021; G06T 2207/20224; G06T 2207/30144; G06T 2207/30168; G06T 2207/30176; G06T 7/0002; G02B 2027/0178; G02B 27/017; G02B 27/0093; G02B 2027/014; G02B 2027/0118; G02B 2027/0187; G02B 27/0172; G02B 5/30; G02B 2027/0138; G02B 27/0176; G02B 2027/0147; G02B 2027/0112; G04G 21/00; G04G 21/08; H03K 17/941; H03K 2217/94104; H03K 2217/94111; H03K 2217/9411; H04W 4/026; H04W 4/027; H04W 4/80; H04W 4/185; H04W 64/00
USPC ......................................... 382/128, 141, 165
See application file for complete search history.

(56) References Cited

U.S. PATENT DOCUMENTS

| | | | |
|---|---|---|---|
| 2002/0036617 A1* | 3/2002 | Pryor | G06F 3/042 345/156 |
| 2006/0025670 A1 | 2/2006 | Kim et al. | |
| 2006/0052684 A1 | 3/2006 | Takahashi et al. | |
| 2009/0097725 A1* | 4/2009 | Krupnik | A61B 1/00096 382/128 |
| 2013/0023899 A1 | 1/2013 | Green | |
| 2013/0127622 A1 | 5/2013 | Choi | |
| 2013/0127980 A1* | 5/2013 | Haddick | G06F 3/013 348/14.08 |
| 2014/0201666 A1* | 7/2014 | Bedikian | G06F 3/017 715/771 |
| 2014/0278220 A1* | 9/2014 | Yuen | G01B 21/16 702/150 |
| 2014/0300722 A1* | 10/2014 | Garcia | G01B 11/02 348/77 |
| 2014/0304629 A1* | 10/2014 | Cummins | A61B 5/742 715/764 |
| 2014/0348403 A1 | 11/2014 | Kurtz et al. | |
| 2015/0043012 A1* | 2/2015 | Rudow | G01S 17/023 356/614 |
| 2015/0080745 A1* | 3/2015 | Wood | A61B 5/0059 600/479 |
| 2015/0150457 A1 | 6/2015 | Wu et al. | |
| 2015/0221077 A1* | 8/2015 | Kawabata | G06T 7/001 382/141 |
| 2015/0301338 A1* | 10/2015 | Van Heugten | G02C 7/04 345/8 |
| 2015/0320513 A1* | 11/2015 | Yoon | G06T 7/0012 600/424 |
| 2015/0379735 A1* | 12/2015 | Lim | G16H 50/20 382/165 |
| 2016/0035096 A1* | 2/2016 | Rudow | G06F 16/51 348/135 |
| 2016/0061588 A1* | 3/2016 | Cho | H04M 1/7253 356/614 |
| 2016/0065832 A1* | 3/2016 | Kim | H04N 5/23212 348/207.11 |
| 2016/0100821 A1* | 4/2016 | Eggers | A61B 8/4254 600/424 |
| 2017/0116725 A1* | 4/2017 | Stuart | G06T 7/0004 |
| 2017/0236273 A1* | 8/2017 | Kim | A61B 5/742 382/128 |
| 2017/0323458 A1* | 11/2017 | Lablans | G01S 19/48 |

FOREIGN PATENT DOCUMENTS

| | | |
|---|---|---|
| JP | 2005-261956 A | 9/2005 |
| KR | 10-1512068 B1 | 4/2015 |
| KR | 10-2015-0061750 A | 6/2015 |
| WO | 03/094768 A1 | 11/2003 |

OTHER PUBLICATIONS

Written Opinion (PCT/ISA/237) dated Apr. 17, 2017 by the International Searching Authority in counterpart International Patent Application No. PCT/KR2015/000751.

\* cited by examiner

1000

100

200

REMOTE IMAGE TRANSMISSION SYSTEM, DISPLAY APPARATUS, AND GUIDE DISPLAYING METHOD THEREOF

CROSS-REFERENCE TO RELATED APPLICATIONS

This application claims priority from Korean Patent Application No. 10-2016-0018533, filed on Feb. 17, 2016 in the Korean Intellectual Property Office, the disclosure of which is incorporated herein by reference in its entirety.

BACKGROUND

Field

Apparatuses and methods consistent with exemplary embodiments relate to a remote image transmission system, a display apparatus, and a guide displaying method thereof, and more particularly, to a remote image transmission system which can provide a physical size regarding a remotely transmitted image, a display apparatus, and a guide displaying method thereof.

Description of the Related Art

In recent years, there has been an increased need and demand for telemedicine, which provides non-face-to-face diagnosis and treatment. In the case of the telemedicine, a doctor makes a diagnosis based on image information transmitted by a patient on a real time basis or a non-real time basis.

In this case, the doctor may have difficulty in obtaining intuitive information, such as patient's height or body type. In addition, there may be a problem that it is difficult to know a size of a patent's specific organ and a real physical size of an affected part. This is because the real size of the affected part occupying the same range on the image varies according to a patient's body size.

In related-art telemedicine, there was an attempt to obtain physical size information. For example, a patient may directly measure the size of an affected part and inform a doctor, or may put a ruler alongside the affected part to measure the size of the affected part. However, this method may cause a burden or inconvenience to patients, and there is a problem that advantages of the telemedicine are reduced.

SUMMARY

One or more exemplary embodiments may overcome the above disadvantages and other disadvantages not described above. However, it is understood that one or more exemplary embodiments are not required to overcome the disadvantages described above, and may not overcome any of the problems described above.

One or more exemplary embodiments provide a remote image transmission system which can display a guide for providing a physical size of a remotely transmitted image with the image, a display apparatus, and a guide displaying method thereof.

According to an aspect of an exemplary embodiment, there is provided a remote image transmission system including: a display apparatus; and an image capturing apparatus including a plurality of image pickup devices that are spaced from each other, the image capturing apparatus being configured to transmit, to the display apparatus, a plurality of images which are captured by the plurality of image pickup devices, wherein the display apparatus is configured to generate a guide object indicating physical information of a captured object by using the plurality of received images, and to display the generated guide object and at least one from among the plurality of images.

According to an aspect of another exemplary embodiment, there is provided a display apparatus including: a communicator configured to communicate with an external device; a display; and a processor configured to generate a guide object indicating physical information of an object included in a plurality of images received from the external device by using the plurality of received images, and to control the display to display the generated guide object and at least one image from among the plurality of received images.

According to an aspect of another exemplary embodiment, there is provided a method for displaying a guide of a display apparatus, the method including: receiving a plurality of images from an external device; generating a guide object indicating physical information of an object included in the plurality of received images; and displaying the generated guide object and at least one image from among the plurality of received images.

Additional and/or other aspects and advantages of the invention will be set forth in part in the description which follows and, in part, will be obvious from the description, or may be learned by practice of the exemplary embodiments.

BRIEF DESCRIPTION OF THE DRAWINGS

The above and/or other aspects will be more apparent by describing certain exemplary embodiments with reference to the accompanying drawings, in which.

DETAILED DESCRIPTION OF THE EXEMPLARY EMBODIMENTS

Exemplary embodiments will be described herein below with reference to the accompanying drawings. In the following description, well-known functions or constructions are not described in detail since they would obscure the present disclosure in unnecessary detail. Also, the terms used herein are defined according to the functions of the exemplary embodiments. Thus, the terms may vary depending on the user's or operator's intention and usage. That is, the terms used herein must be understood based on the descriptions made herein.

The terms such as "first" and "second" used in various exemplary embodiments may be used to explain various elements, and does not limit the corresponding elements. These terms may be used for the purpose of distinguishing one element from another element. For example, a first element may be referred to as a second element without departing from the scope of right of various exemplary embodiments, and similarly, a second element may be referred to as a first element. The term "and/or" may include a combination of a plurality of relevant items or any one of the plurality of relevant items.

The terms used in various exemplary embodiments are just for the purpose of describing particular exemplary embodiments, and are not intended to limit the present disclosure. As used herein, the singular forms are intended to include the plural forms as well, unless the context clearly indicates otherwise. The terms "include" and "have" used in the exemplary embodiments indicate the presence of features, numbers, operations, elements, or components described in the specification or a combination thereof, and do not preclude the presence or addition of one or more other features, numbers, operations, elements, or components or a combination thereof.

Figure 1:
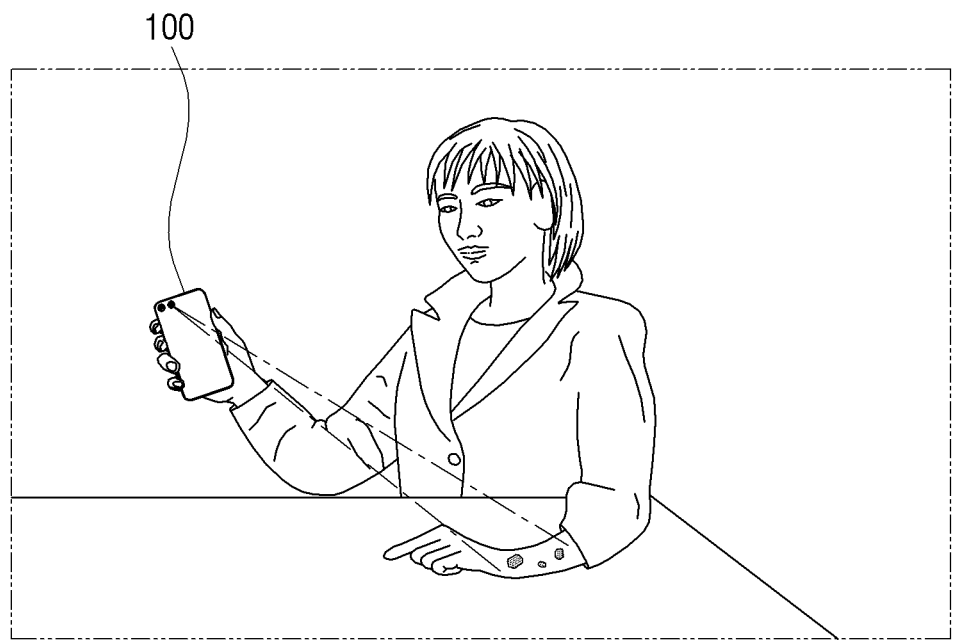
FIG. 1 is a concept view to illustrate a remote image transmission system, according to an exemplary embodiment.
Figure 1:
Figure 1:
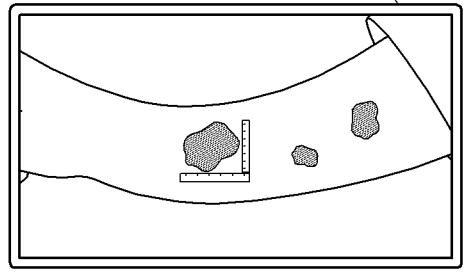
Figure 1:

FIG. 1 is a concept view to illustrate a remote image transmission system 1000, according to an exemplary embodiment. Referring to FIG. 1, the remote image transmission system 1000 may include an image capturing apparatus 100 and a display apparatus 200. In FIG. 1, the image capturing apparatus 100 is illustrated as a smart phone that includes a dual camera, and the display apparatus 200 is illustrated as a smart television (TV). However, the image capturing apparatus 100 and the display apparatus 200 are not limited to these.

The remote image transmission system 1000 according to an exemplary embodiment may be used in a field where there is a need to know a size of an object included in a captured image. The telemedicine field as shown in FIG. 1 is a representative example of the field in which the remote image transmission system 1000 according to an exemplary embodiment can be used. The telemedicine refers to the provision of non-face-to-face treatment which is performed between a patient and a doctor based on patient-specific information that is transmitted via images. Referring to FIG. 1, the remote image transmission system 1000 according to an exemplary embodiment displays a guide object that provides information relating to a size of an affected area in conjunction with an image of the affected area captured by the patient, such that the doctor can provide accurate medical treatment.

The image capturing apparatus 100 may capture an object by using a plurality of image pickup devices, and provide physical information of the captured image to the display apparatus in conjunction with the captured image. Alternatively, the image capturing apparatus 100 may not provide the physical information of the captured image and may provide information from which the physical information may be determined. For example, the image capturing apparatus 100 may provide a distance between the plurality of image pickup devices and focal distance information, instead of directly providing information on the size of the captured object.

The image capturing apparatus 100 may be implemented by using a smart phone that includes a dual camera, a tablet personal computer (PC), a wearable device such as smart glasses, a digital camera, or the like. The image capturing apparatus 100 may provide the captured image in the form of a moving image or a still image. In addition, the image capturing apparatus 100 may provide the captured moving image in the form of a live view on a real time basis.

The display apparatus 200 may be implemented by using a smart TV, a monitor, a smart phone, a tablet PC, or the like. The display apparatus 200 may receive a plurality of images captured by the image capturing apparatus 100 and information that includes physical information. In addition, the display apparatus 200 may generate a guide object indicating the physical information of the captured object. For example, the display apparatus 200 may generate size information of the object included in the received image by using the distance between the plurality of image pickup devices and the focal distance of each image pickup device. In addition, the display apparatus 200 may display the received image in conjunction with the generated guide object. Referring to FIG. 1, the display apparatus 200 may display the image of the patient's arm received and a guide object in the form of a ruler which reveals the size of the affected area.

According to the remote image transmission system 1000 according to an exemplary embodiment as described above, the physical information of the object included in the image can be intuitively provided by using the captured image and hardware information of the image capturing apparatus, without separately measuring physical information.

Hereinafter, the configuration and operation of the image capturing apparatus 100 and the display apparatus 200 of the remote image transmission system 1000 will be described in detail with reference to the drawings.

Figure 2:
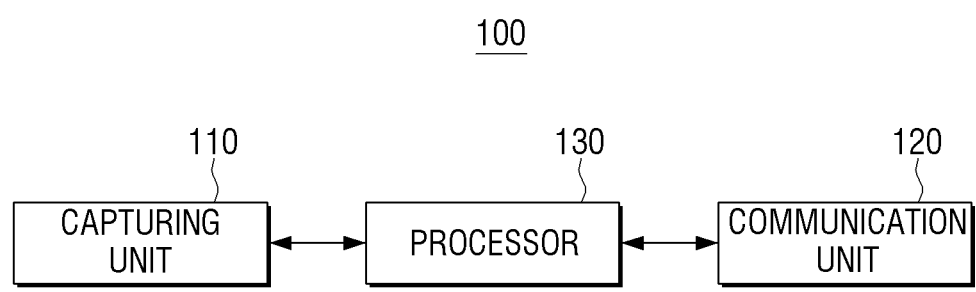
FIG. 2 is a block diagram to illustrate a configuration of an image capturing apparatus, according to an exemplary embodiment.

FIG. 2 is a block diagram to illustrate the configuration of the image capturing apparatus 100, according to an exemplary embodiment. Referring to FIG. 2, the image capturing apparatus 100 may include a capturing unit (also referred to herein as a "capturer") 110, a communication unit (also referred to herein as a "communicator" and/or as a "transceiver") 120, and a processor 130. The image capturing apparatus 100 may further include a memory (not shown), a display (not shown), and an inputter (not shown), which are not illustrated in FIG. 2, and is not limited as having only the elements shown in FIG. 2.

Figure 3:
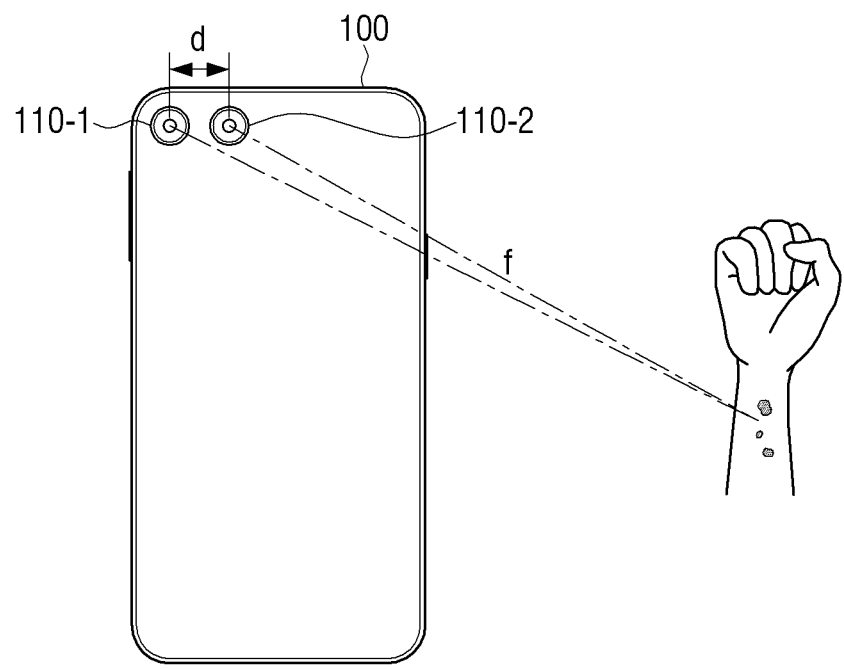
FIG. 3 is a view to illustrate information which is obtained by a plurality of image pickup devices of the image capturing apparatus, according to an exemplary embodiment.

The capturing unit 110 may generate an image by capturing an object. In addition, the capturing unit 110 may include a plurality of image pickup devices spaced from one another. For example, the capturing unit 110 may be implemented in the form of a dual camera including two image pickup devices 110-1 and 110-2 as shown in FIG. 3. In addition, the capturing unit 110 may capture a stereo image using the two image pickup devices of the dual camera.

The communication unit 120 may communicate with the display apparatus 200 in a wired or wireless manner. For example, the communication unit 120 may transmit a plurality of captured images to the display apparatus 200. In addition, the communication unit 120 may transmit specification information of the image pickup devices, a model name of the image capturing apparatus 100, or the like with the captured images. In the example of FIG. 3, the communication unit 120 may transmit information relating to a distance (d) between the plurality of image pickup devices 110-1 and 110-2 and a focal distance (f) of the image pickup device.

For example, the communication unit 120 may use any of various wireless communication methods, such as Near Field Communication (NFC), a wireless Local Area Network (LAN), Infrared (IR) communication, Zigbee communication, wireless fidelity (WiFi), Bluetooth, or the like. In addition, the communication unit 120 may use any of various wire communication methods, such as a High Definition Multimedia Interface (HDMI), Low Voltage Differential Signaling (LVDS), a LAN, a Universal Serial Bus (USB), or the like.

The processor 130 controls the overall operation of the image capturing apparatus 100. For example, the processor 130 may control the communication unit 120 to transmit information on the distance between the plurality of image pickup devices and the focal distance of each image pickup device with the plurality of captured images.

In another example, the processor 130 may generate a guide object indicating size information of the captured object by using the information on the distance between the plurality of image pickup devices and the focal distance of each image pickup device. In addition, the processor 130 may control the communication unit 120 to transmit the generated guide object with the plurality of captured images.

The image capturing apparatus 100 according to an exemplary embodiment may capture an image using a specific wavelength, in addition to capturing a normal image. For example, the image capturing apparatus 100 may further include a light source (not shown) for providing light of a predetermined wavelength. In addition, at least one of the plurality of image pickup devices included in the capturing unit 110 may receive reflected light occurring as a result of the light of the predetermined wavelength provided by the light source (not shown). For example, the light source (not shown) may provide light of an infrared wavelength, and at least one of the plurality of image pickup devices may be an infrared image sensor or an infrared camera.

Figure 4:
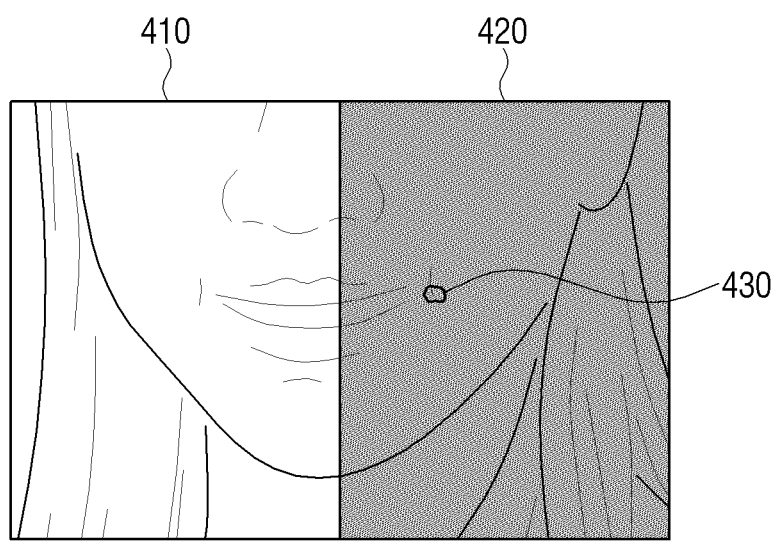
FIG. 4 is a view showing a normal image and an image which is captured using a specific wavelength, according to an exemplary embodiment.

FIG. 4 is a view showing a normal image 410 and an image 420 which is captured using a specific wavelength, according to an exemplary embodiment. In an exemplary embodiment in which a skin disease is remotely diagnosed by using the remote image transmission system 1000 as shown in FIG. 4, it may be difficult to distinguish between ringworm caused by a fungus and a normal skin disease based on the normal image 410. Use of a steroid for external use for treating a normal skin disease may aggravate the ringworm caused by the fungus. To prevent this problem, an image which is captured using a specific wavelength may be obtained. Using the characteristic that the fungus reflects a specific wavelength, the image capturing apparatus 100 may project light of a predetermined wavelength onto the patient's skin, collect reflected light, and generate a special capture image 420. Referring to FIG. 4, an area 430 of the ringworm caused by the fungus may be captured on the special capture image 420. In addition, the processor 130 may control the communication unit 120 to transmit the captured normal image 410 and the special capture image 420 to the display apparatus 200.

The image capturing apparatus 100 may store information indicating which wavelength of light should be projected to diagnose a specific disease. Alternatively, the image capturing apparatus 100 may receive a control command to project light of a specific wavelength and capture a special image from the display apparatus 200.

According to another exemplary embodiment, the image capturing apparatus 100 in which at least one of the plurality of image pickup devices is an infrared camera may capture an infrared image, and then use the captured infrared image to improve performance of recognition of a vein pattern or an iris.

According to an exemplary embodiment, the processor 130 may control the capturing unit 110 such that the plurality of image pickup devices capture images at the same time. In another example, the processor 130 may control the capturing unit 110 such that the plurality of image pickup devices capture images alternately at different respective times.

Figure 5:
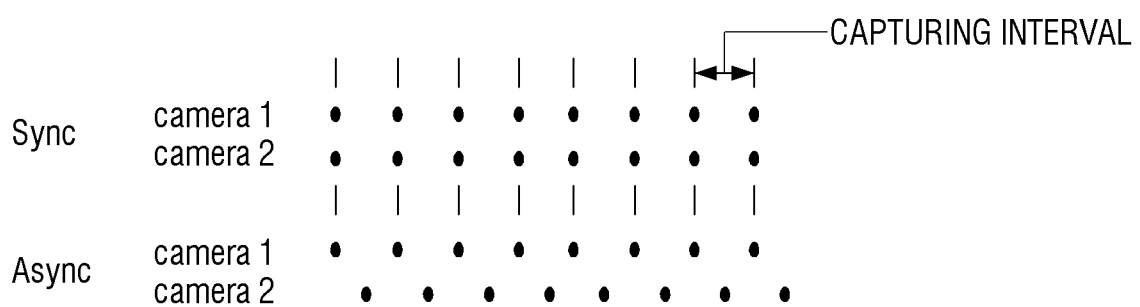
FIG. 5 is a view to illustrate image capturing timing in the image capturing apparatus, according to an exemplary embodiment.

FIG. 5 is a view showing image capturing point times (frame capturing times) in the image capturing apparatus 100, according to an exemplary embodiment. In FIG. 5, it is assumed that the capturing unit 110 includes two cameras.

First, in a sync mode illustrated in the upper portion of FIG. 5, the processor 130 may control the capturing unit 110 such that the camera 1 and the camera 2 capture images at the same time. For example, when the camera 1 and the camera 2 of the capturing unit 110 are able to capture 30 frames per second, the processor 130 may control each of the cameras 1 and 2 to capture 30 frames per second in synchronization with each other.

When there is a need to closely observe a motion of an object to be captured, the processor 130 may control the camera 1 and the camera 2 to capture images alternately. In an asynchronize mode illustrated in the lower portion of FIG. 5, image capturing times of the camera 1 and the camera 2 alternately arrive. Accordingly, by controlling the image capturing times of the capturing unit 110 which is able to capture 30 frames per second, the processor 130 may generate an image based on an effective capture rate of 60 frames captured per second.

According to an exemplary embodiment, the processor 130 may control the capturing unit 110 to capture an image in the sync mode during a predetermined time interval at the beginning of the image capturing operation. In addition, the processor 130 may control the capturing unit 110 to capture an image in the asynchronize mode during a predetermined time interval after capturing in the sync mode. The capturing in the sync mode may provide physical information such as a size/distance of an object. In addition, the capturing in the asynchronize mode may provide information on a minute motion of the object.

Figure 6:
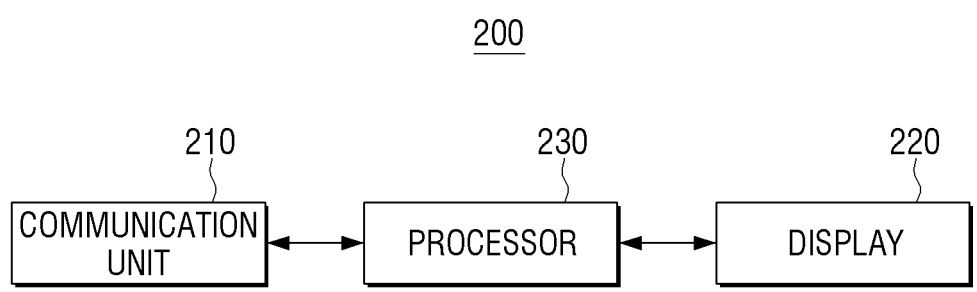
FIG. 6 is a schematic block diagram showing a configuration of a display apparatus, according to an exemplary embodiment.

FIG. 6 is a schematic block diagram to illustrate the configuration of the display apparatus 200, according to an exemplary embodiment. Referring to FIG. 6, the display apparatus 200 may include a communication unit (also referred to herein as a "communicator" and/or as a "transceiver") 210, a display 220, and a processor 230.

The communication unit 210 may communicate with the image capturing apparatus 100 in a wire or wireless manner. For example, the communication unit 210 may receive a plurality of captured images from the image capturing apparatus 100. In addition, the communication unit 210 may receive the specification information of the image pickup devices (for example, a distance between the image pickup devices and a focal distance of the image pickup device), the model name of the image capturing apparatus 100, or the like, in conjunction with the captured images. The communication unit 210 may transmit the model name of the image capturing apparatus 100 to an external server (not shown) and may receive specification information corresponding to the model name from the external server.

The display 220 may display an image, an object, or the like. For example, the display 220 may display at least one of the plurality of received images. In addition, the display 220 may display a generated guide object, a graphic object, or the like in conjunction with the received image. In addition, the display 220 may display a button for controlling to generate a guide object of a specific form in the form of a guide user interface (GUI).

The processor 230 may generate a guide object indicating physical information of a captured object by using the plurality of received images. The processor 230 may generate physical information of the captured object, such as a size, by using the specification information of the image capturing apparatus 100. In addition, the processor 230 may control the display 220 to display the generated guide object with at least one of the plurality of received images.

The processor 230 may generate an estimated error range when generating the physical information. For example, an error may occur due to physical limitations (for example, a nearest distance depending on a focal distance, or a limit of a computable minimum value) caused by an image capturing environment, an image capturing condition, and the specification information of the image capturing apparatus 100. The processor 230 may provide the estimated error range information to the user, so that the estimated error range information may be helpful with respect to providing an accurate diagnosis.

The processor 230 may detect an area which can be distinguished from a background area, such as, for example, an affected area, from at least one image of the plurality of received images. In addition, the processor 230 may generate a graphic object to surround the detected area. In addition, the processor 230 may control the display 220 to display the generated graphic object in conjunction with at least one image of the plurality of received images.

Figure 7:
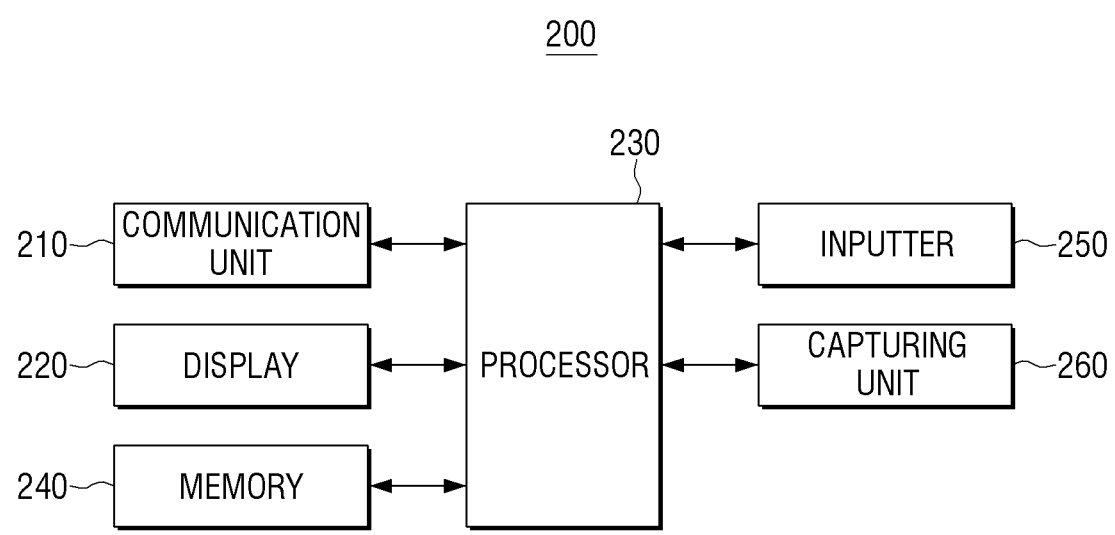
FIG. 7 is a block diagram to illustrate the configuration of the display apparatus in detail, according to an exemplary embodiment.

FIG. 7 is a block diagram to illustrate the configuration of the display apparatus 200 in detail, according to an exemplary embodiment. Referring to FIG. 7, the display apparatus 200 may further include a memory 240, an inputter 250, and a capturing unit 260, in addition to the communication unit 210, the display 220, and the processor 230. However, the display apparatus 200 according to an exemplary embodiment is not limited to necessarily including the elements shown in FIG. 7 or not including other elements. For example, the display apparatus 200 may not include the capturing unit 260. In addition, the display apparatus 200 may further include an audio outputter (not shown).

The communication unit 210 may communicate with an external device. For example, the communication unit 210 may communicate with the image capturing apparatus 100 to receive captured images. In addition, the communication unit 210 may receive at least one of the specification information and the model name of the image capturing apparatus 100.

For example, the communication unit 210 may use any of various wireless communication methods, such as NFC, a wireless LAN, IR communication, Zigbee communication, WiFi, Bluetooth, or the like. In addition, the communication unit 210 may use any of various wire communication methods, such as a HDMI, LVDS, a LAN, a USB, or the like.

In addition, the communication unit 210 may exchange data with a hospital server which is connected via the Picture Archiving and Communication System (PACS) or with other medical devices in the hospital. In addition, the communication unit 210 may communicate data according to the Digital Imaging and Communications in Medicine (DICOM) standard.

The display 220 may display the received image, the generated guide object, and a GUI for enabling a user to input a user command.

The method of implementing the display 220 is not limited. For example, the display 220 may be implemented by using any of various types of displays, such as a Liquid Crystal Display (LCD), an Organic Light Emitting Diode (OLED), Active-Matrix (AM)-OLED, a Plasma Display Panel, or the like. The display 220 may further include an additional configuration according to an implementation method. For example, when the display 220 is implemented by using an LCD, the display 220 may include an LCD panel (not shown), a backlight unit (not shown) to provide light to the LCD panel, and a panel driving substrate (not shown) for driving the panel (not shown).

The display 220 may be implemented in the form of a touch screen which forms an inter-layer structure with a touch pad, and the touch screen may receive a user command via a touch input location, a touch area, and/or a pressure of a touch input. In this case, the display 220 may perform the function of the inputter 250.

The display 220 may be implemented in the form of a bended (i.e., bent) display and may be connected with at least one of a front area, a side area, or a rear area of the display apparatus 200. The bended display may be implemented using a flexible display or may be implemented by using a normal display which is not flexible. For example, the bended display may be implemented by connecting a plurality of flat displays with one another.

The memory 240 may store various programs and data necessary for the operation of the display apparatus 200. The memory 240 may be implemented by using any of a flash memory, a hard disk, or the like. For example, the memory 240 may include a Read Only Memory (ROM) for storing programs for performing the operation of the display apparatus 200, and/or a Random Access Memory (RAM) for temporarily storing data generated by performing the operation of the display apparatus 200. In addition, the memory 240 may further include an Electrically Erasable and Programmable ROM (EEPROM) for storing various reference data.

The memory 240 may store programs and data for configuring various screens to be displayed on the display 220. In addition, the memory 240 may store programs and data for performing a specific service. For example, the memory 240 may store specification information corresponding to the model name of the image capturing apparatus 100. In addition, the memory 240 may store wavelength information of light to be projected in order to facilitate a diagnosis of a specific disease. In addition, the memory 240 may store a pre-generated graphic object with information relating to when the graphic object was generated.

The inputter 250 may receive a request, a command, or other data for controlling the operation of the display apparatus 200 from the user. For example, the inputter 250 may receive a user command to select one of a plurality of objects included in a displayed image. The inputter 250 may be implemented by using any one or more of a keypad, a mouse, a touch panel, a touch screen, a track ball, a jog switch, or the like.

The capturing unit 260 may include a plurality of image pickup devices spaced from one another. In addition, the capturing unit 260 may generate a plurality of images captured by the plurality of image pickup devices. According to an exemplary embodiment, the display apparatus 200 may implement augmented reality (AR) by combining an image generated in the capturing unit 260 thereof with an image received from the image capturing apparatus 100.

The processor 230 may control the overall operation of the display apparatus 200. The processor 230 may generate a guide object indicating physical information of a captured object by using the plurality of received images. The processor 230 may generate physical information of a captured object, such as a size, by using the specification information of the image capturing apparatus 100. In addition, the processor 230 may control the display 220 to display the generated guide object in conjunction with at least one of the plurality of received images.

Figure 8:
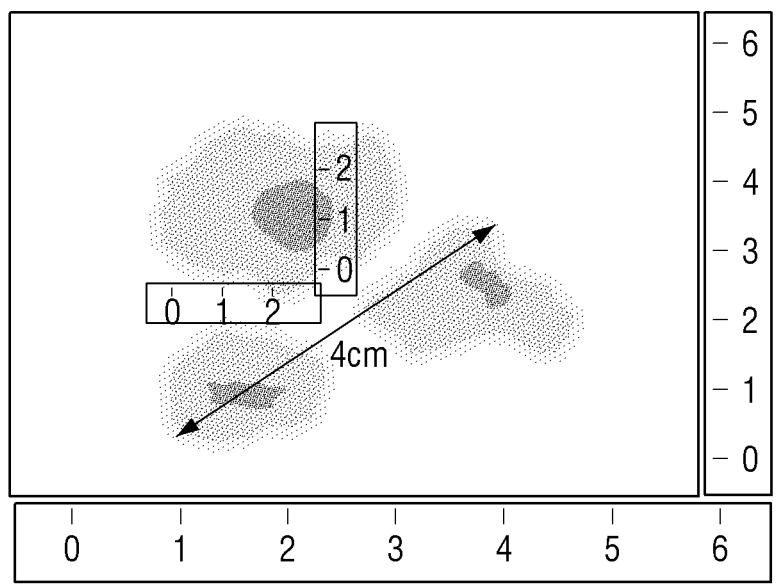
FIGS. 8, 9 and 10 are views to illustrate a guide object according to an exemplary embodiment.
Figure 9:
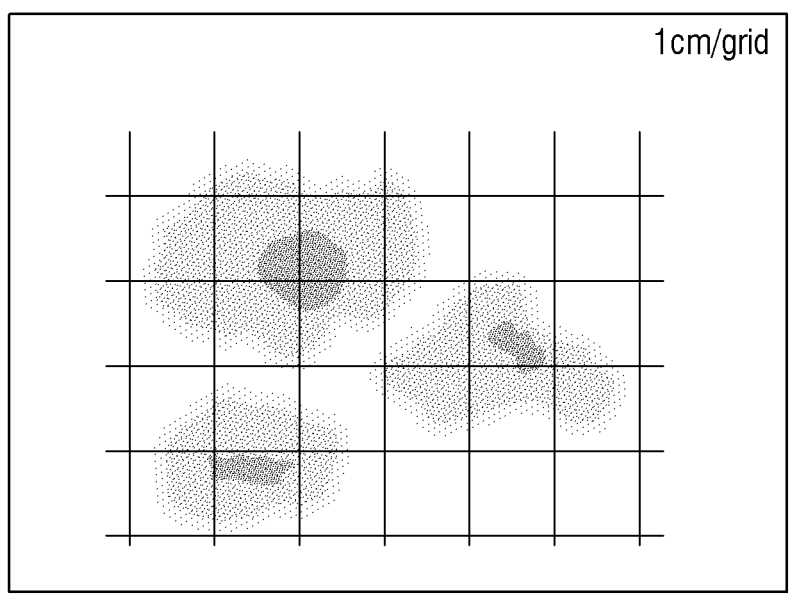
Figure 10:
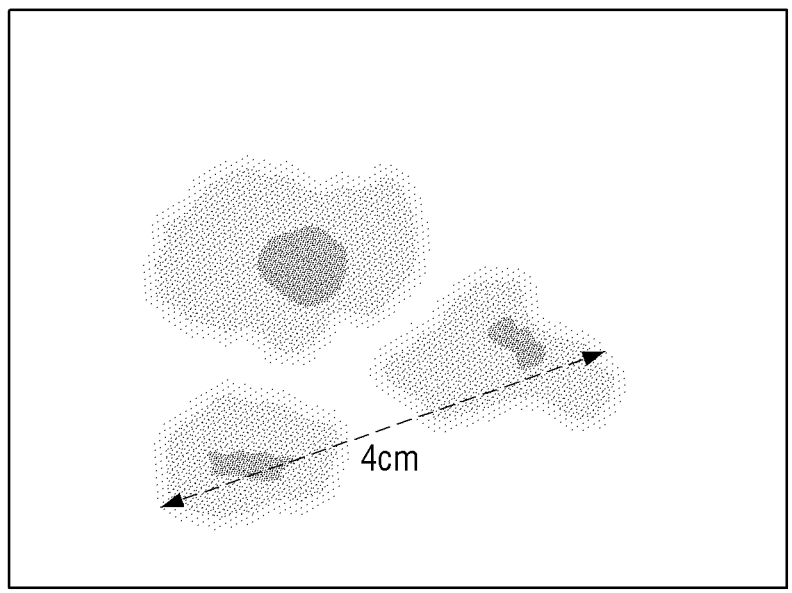

According to an exemplary embodiment, the processor 230 may generate the guide object in the form of at least one of a ruler, a grid, and an arrow. FIGS. 8, 9, and 10 are views illustrating a screen on which a guide object is displayed with a received image, according to various exemplary embodiments.

Referring to FIG. 8, the processor 230 may generate a guide object indicating size information of a captured affected area. In FIG. 8, the processor 230 may generate a guide object in the form of a ruler providing length information. In addition, the processor 230 may control the display 220 to display a first ruler guide object on the outer border of the image together with the received image. In addition, the processor 230 may detect the affected area and control the display 220 to display a second ruler guide object for determining size information on the periphery of the detected affected area. As an arrow guide object indicating a diameter of the affected area is displayed in FIG. 8, the guide object is not necessarily provided only in a single form, but instead may be provided in a plurality of forms.

Referring to FIG. 9, the processor 230 may generate a guide object in the form of a grid indicating size information of a captured image. The processor 230 may control the display 220 to display the guide object in the form of the grid together with the received image. In addition, the processor 230 may also provide information on length of one side of each square. For example, as illustrated in FIG. 9, the provided information may indicate that the length of one side of each grid square is equal to one centimeter (1 cm).

Referring to FIG. 10, the processor 230 may generate a guide object in the form of an arrow providing distance information between specified points of a received image. The guide object in the form of the arrow may include a text indicating the length of the arrow. For example, in response to a reception of a user command to select specific points of the displayed image, the processor 230 may generate a guide object in the form of an arrow connecting the selected points, and provide corresponding physical information. For example, as illustrated in FIG. 10, the provided physical information may indicate that the distance between the specified points is equal to four centimeters (4 cm). In another example, the processor 230 may generate a guide object in the form of an arrow corresponding to a diameter of a detectable area without receiving a user command to select specific points.

Figure 11:
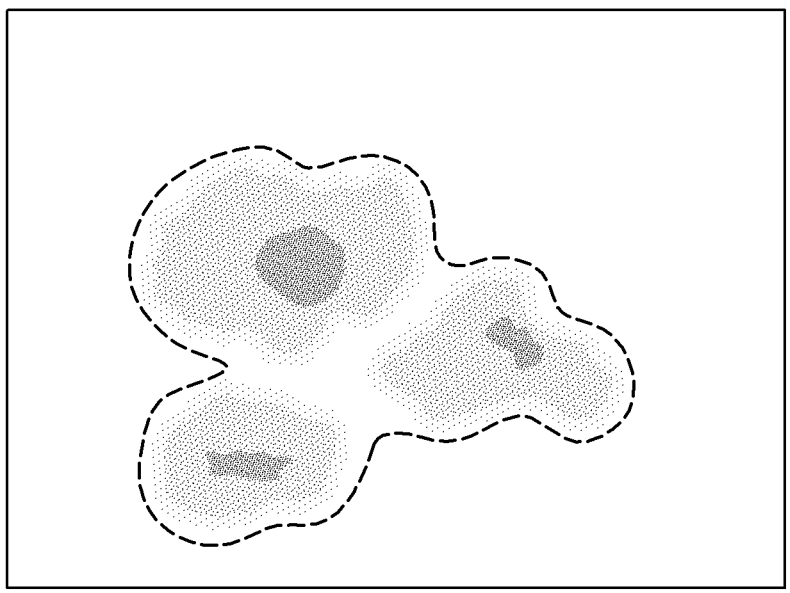
FIG. 11 is a view illustrating a graphic object surrounding an affected area, according to an exemplary embodiment.

According to an exemplary embodiment, the processor 230 may detect an area which can be distinguished from a background area, like an affected area, from at least one image of a plurality of received images. In addition, the processor 230 may generate a graphic object to surround the detected area. In addition, the processor 230 may control the display 220 to display the generated graphic object in conjunction with at least one of the plurality of received images. As shown in FIG. 11, the processor 230 may detect an affected area from a received image, and then generate a graphic object in the form of a closed curve surrounding the affected area. The graphic object surrounding the detected area may be implemented in any of various shapes, such as a circle, a rectangle, or the like, in addition to the closed curve.

Figure 12:
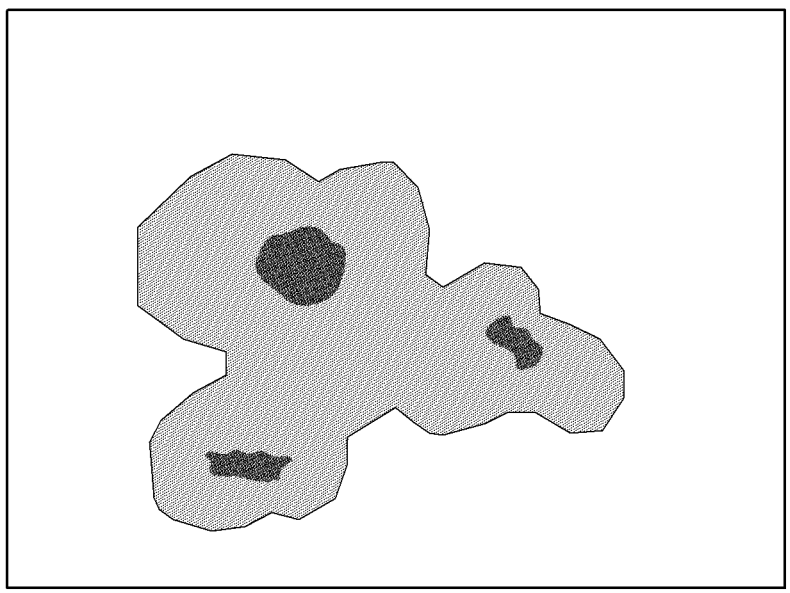
FIG. 12 is a view illustrating a result of filtering on an affected area, according to an exemplary embodiment.

According to an exemplary embodiment, the processor 230 may perform filtering to change an image characteristic of the detected area (for example, an affected area). When the detected area is not easily distinguishable from the background area with the naked eye, visual processing for highlighting the detected area may be required. As shown in FIG. 12, the processor 230 may perform filtering or another image processing function, such as, for example, changing a contrast, in order to highlight the detected affected area.

Figure 13:
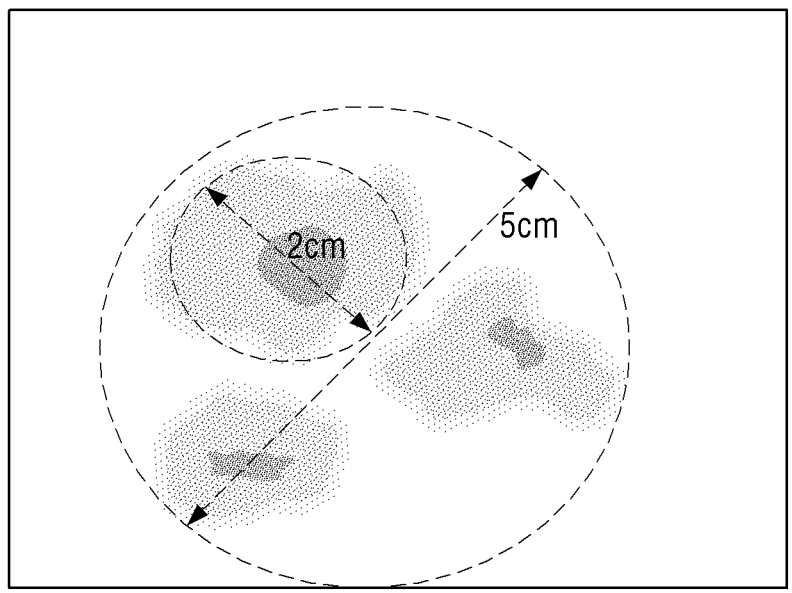
FIG. 13 is a view displaying size information of an affected area, according to an exemplary embodiment.

As shown in FIG. 13, the processor 230 may generate a graphic object surrounding the detected affected area. In addition, the processor 230 may store the generated graphic object in the memory 240 together with time information in order to track a change with time.

In addition, the processor 230 may control the display 220 to display a graphic object surrounding a current affected area with a graphic object which has previously been generated regarding an affected area detected from within a previously received image and stored.

Figure 14:
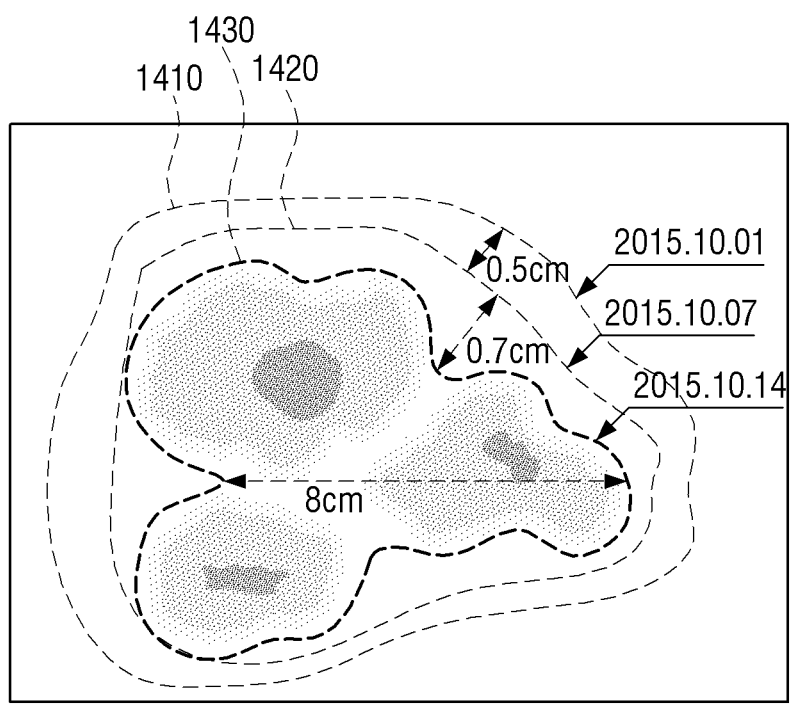
FIG. 14 is a view showing graphic objects for comparing results of tracking changes in the affected area, according to an exemplary embodiment.

FIG. 14 is a view to illustrate graphic objects for comparing results of tracking a change in an affected area, according to an exemplary embodiment. Referring to FIG. 14, the processor 230 may control the display 220 to display an image currently received on Oct. 14, 2015 and a graphic object 1430 surrounding a detected affected area. In addition, the processor 230 may control the display 220 to display graphic objects 1410 and 1420 which had previously been generated regarding the affected area as detected on Oct. 1, 2015 and Oct. 7, 2015 and stored.

In addition, the processor 230 may generate a guide object for providing distance information between the plurality of graphic objects 1410, 1420, and 1430 and may also provide the guide object. In the example of FIG. 14, a distance between the graphic object 1410 generated on October 1 and the graphic object 1420 generated on October 7 is equal to 0.5 cm, and a distance between the graphic object 1420 generated on October 7 and the graphic object 1430 generated on October 14 is equal to 0.7 cm.

In order to exactly provide a change as described above, the locations of the graphic objects that were previously generated and the location of the graphic object that is currently generated should match each other.

According to an exemplary embodiment, the processor 230 may extract a characteristic point from within a received image. For example, the characteristic point may be a tip of a nose, a corner of a mouth, a location of wrinkles, a pattern of a spot, or the like. Since a distance to an object to be captured changes every time capturing is performed in the image capturing apparatus 100, the display apparatus 200 according to an exemplary embodiment may extract a characteristic point from a received image and may use the characteristic point as a reference point for matching, in order to ensure that images captured at different capturing times have the same size.

Figure 15A:
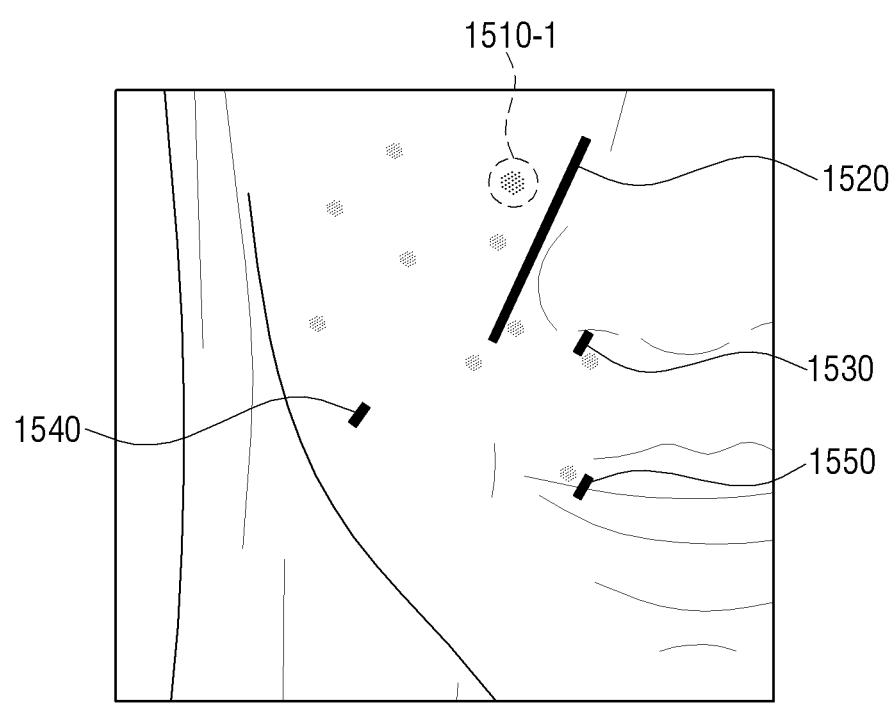
FIGS. 15A and 15B are views to illustrate a method for detecting a characteristic point, according to an exemplary embodiment.
Figure 15B:
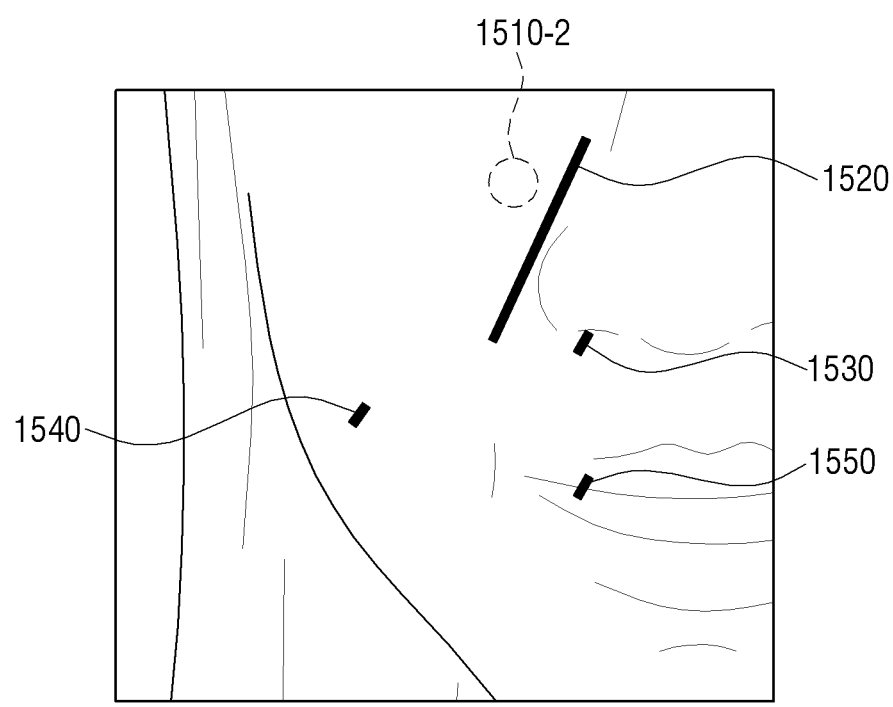

FIGS. 15A and 15B are views to illustrate a method for detecting a characteristic point, according to an exemplary embodiment. Referring to FIGS. 15A and 15B, the processor 230 may detect a ridge of a nose 1520, a tip of the nose 1530, a spot 1540, and a corner of a mouth 1550 as characteristic points. In addition, using the detected characteristic points 1520, 1530, 1540, and 1550, the processor 230 may determine a location 1510-2 as illustrated in FIG. 15B regarding an area 1510-1 having an infection, as illustrated in FIG. 15A.

Figure 16:
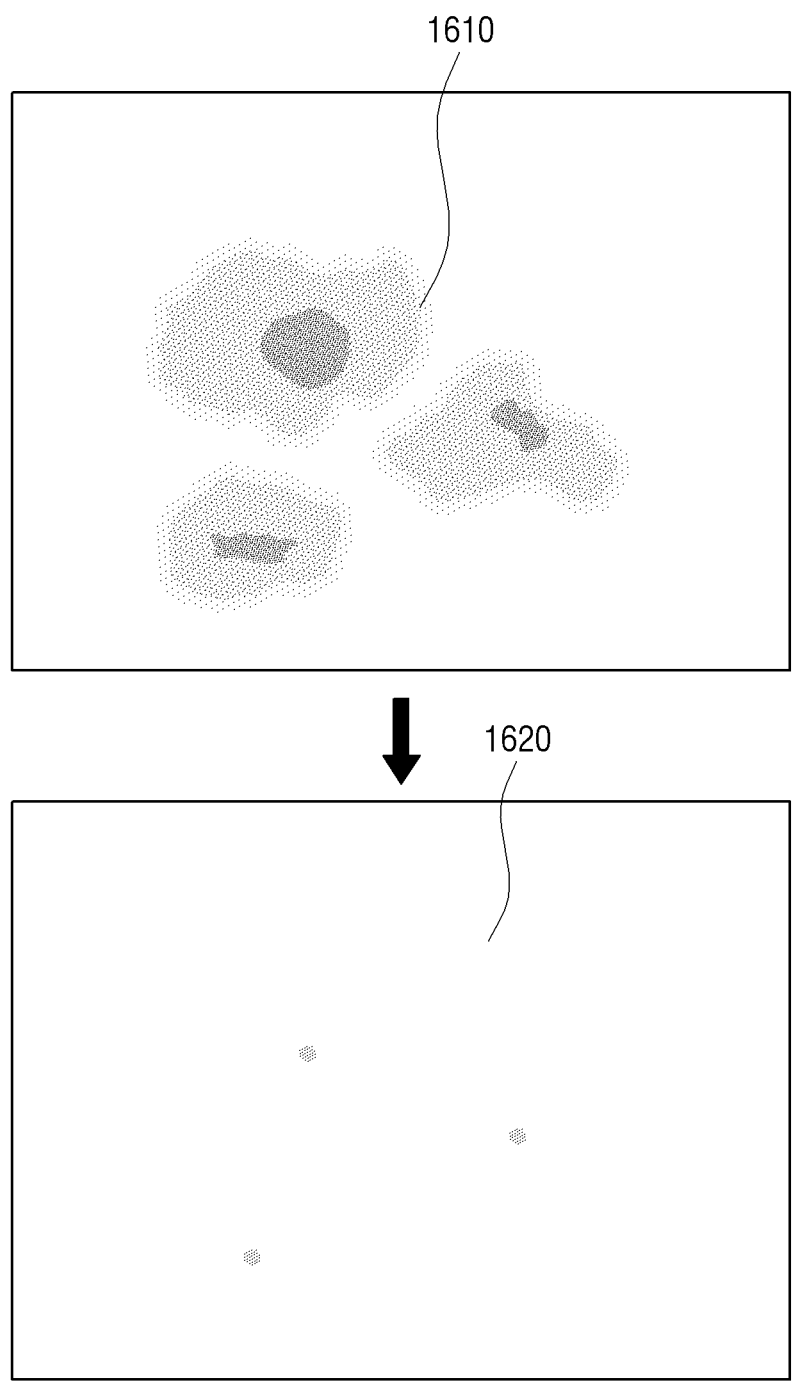
FIG. 16 is a view to illustrate generating an estimated image of an affected area, according to an exemplary embodiment.

According to an exemplary embodiment, the processor 230 may generate an estimated future image of the affected area by tracking the change in the detected affected area. Referring to FIG. 16, the processor 230 may calculate a change by comparing the size of an affected area 1610 of a currently received image with the sizes of the graphic objects surrounding the affected area in previously received images, which are stored. In addition, the processor 230 may generate the estimated future image 1620 of the affected area by using the calculated change.

The guide object provided with physical information, such as size information, is not needed only for a diagnosis which is made with an image on a plane, such as, for example, a diagnosis of a skin disease. For example, in the case of a diagnosis requiring three-dimensional (3D) information, such as swelling occurring on an eye, wrist, angle, or calf, bending caused by a fracture of a finger or a nose, or an affected area caused by a stab, the remote image transmission system 1000 according to an exemplary embodiment may be used.

Figure 17:
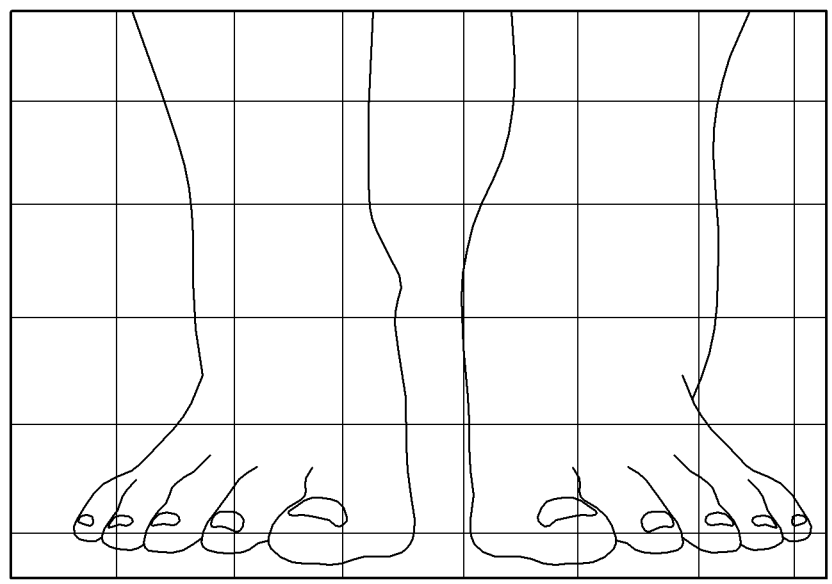
FIGS. 17 and 18 are views to illustrate a guide object, according to an exemplary embodiment.

According to an exemplary embodiment, in order to identify a difference in the swelling between both ankles, the processor 230 may control the display 220 to display a guide object in the form of a grid, as shown in FIG. 17.

Figure 18:
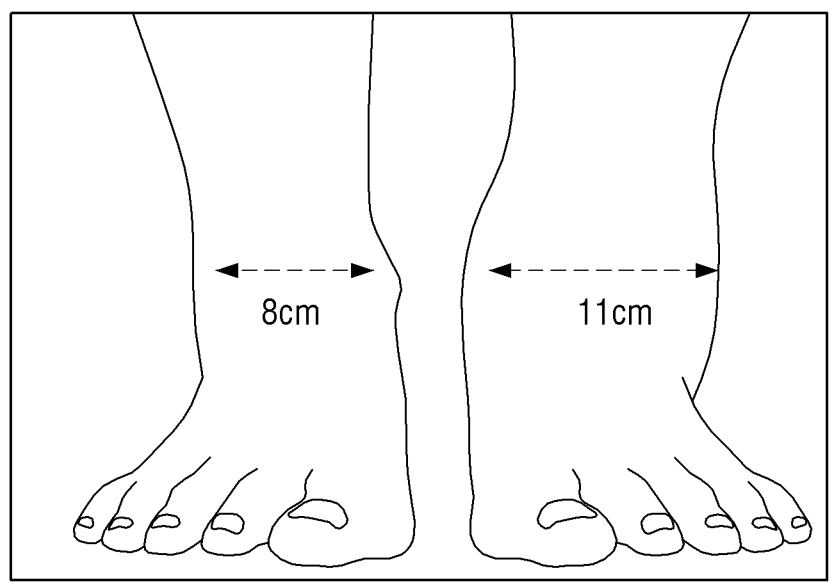

In another example, in response to a user command to select an object being received via the inputter 250, the processor 230 may generate a guide object for displaying size information of the selected object. Referring to FIG. 18, in response to a user command to select one point of both ankles as objects included in an image, the processor 230 may generate a guide object providing distance information corresponding to a horizontal direction with respect to the selected point. In this case, the processor 230 may generate distance information by using 3D information. Since the distance information is generated by using the 3D information, the coordinate system is robustly maintained even when there is a rotation or a translation, and thus the processor 230 can generate exact distance information.

Figure 19A:
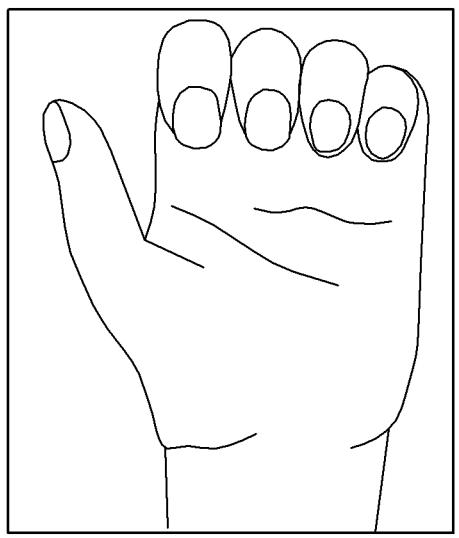
FIGS. 19A, 19B, and 19C are views to illustrate generating and manipulating a three-dimensional (3D) model, according to an exemplary embodiment.
Figure 19B:
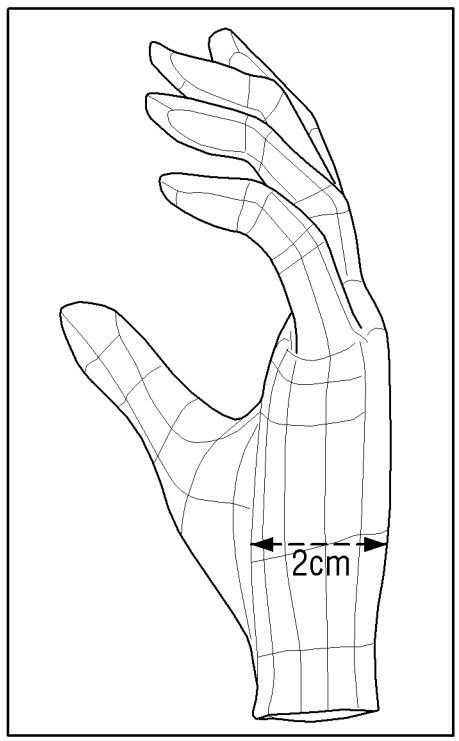
Figure 19C:
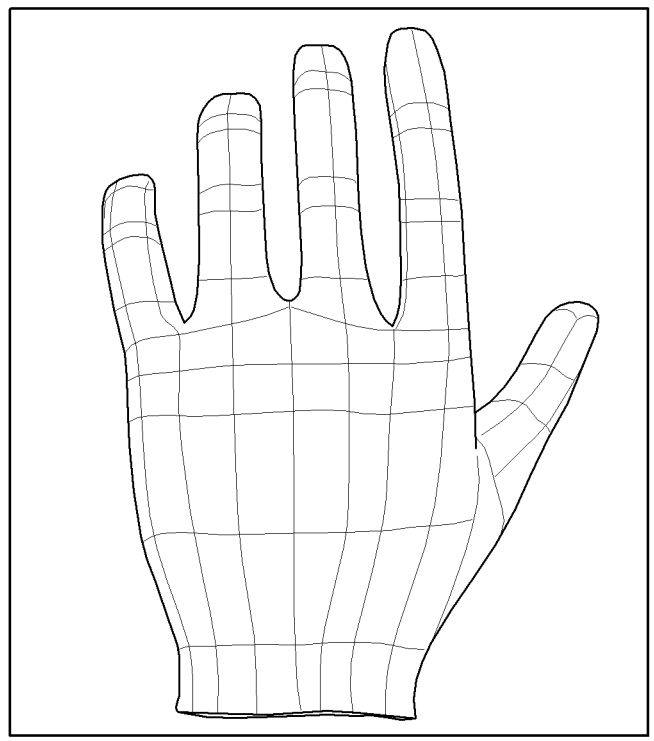

FIGS. 19A, 19B, and 19C are views to illustrate generating and manipulating a 3D model, according to an exemplary embodiment. The processor 230 may generate a 3D model of an object included in a plurality of images by using a plurality of received images. Since the image capturing apparatus 100 according to an exemplary embodiment captures an object by using the plurality of image pickup devices which are spaced from each other, the image capturing apparatus 100 may obtain depth information or the like that is necessary for generating the 3D model. Using a plurality of captured images of one hand as shown in FIG. 19A, the processor 230 may generate a 3D model as shown in FIG. 19B. In addition, the processor 230 may control the display 220 to display a guide object indicating size information on the 3D model. In addition, the processor 230 may perform a manipulation, such as, for example, rotating the 3D model as shown in FIG. 19C. In this manner, the user can be provided with the exact shape and size of the object.

According to the remote image transmission system 1000 as described above, in a remote medical treatment field, the user can recognize the size information of an affected area without directly measuring it, as would usually be done in the course of real face-to-face treatment. Accordingly, there are advantages that only a minimum motion of a patient is required and an accurate diagnosis can be made.

The remote image transmission system 1000 according to an exemplary embodiment can be applied to any field that should provide size information of an image, similarly as with respect to the remote medical treatment field. For example, in an online clothing sales field, it may be difficult to know a size of a particular article of clothing based solely upon a clothing image. Accordingly, exact size information may be provided with a clothing image by using the remote image transmission system 1000 according to an exemplary embodiment.

Figure 20A:
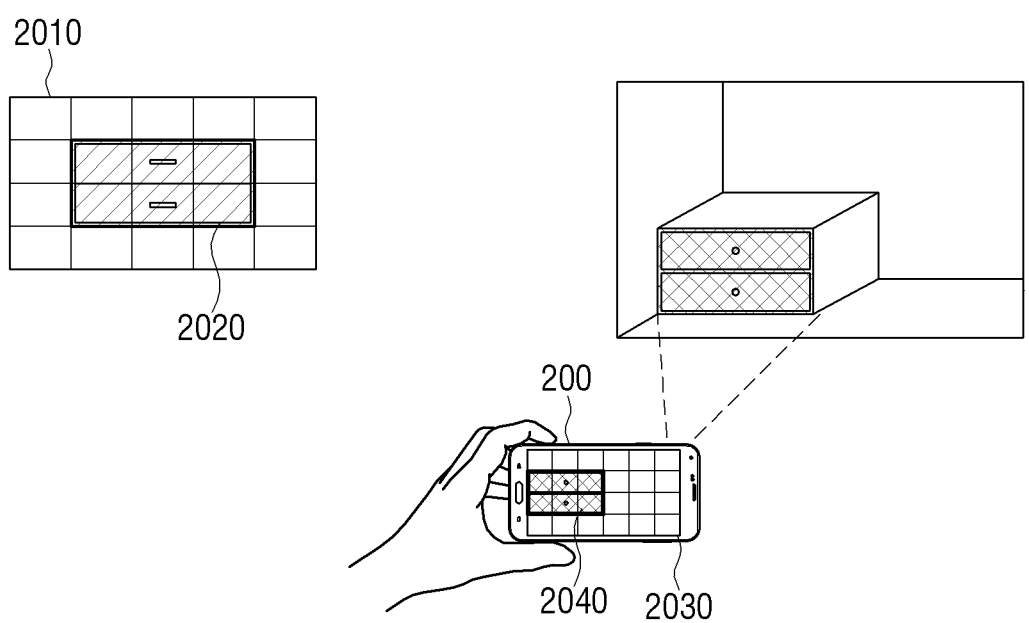
FIGS. 20A, 20B, and 20C are views to illustrate a method for matching a size of a live view image and a size of a received image, according to another exemplary embodiment.
Figure 20B:
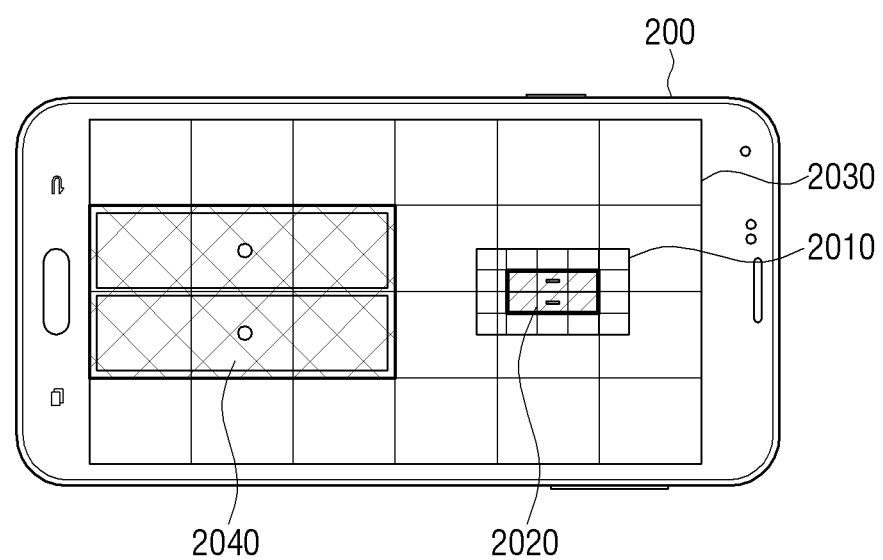
Figure 20C:
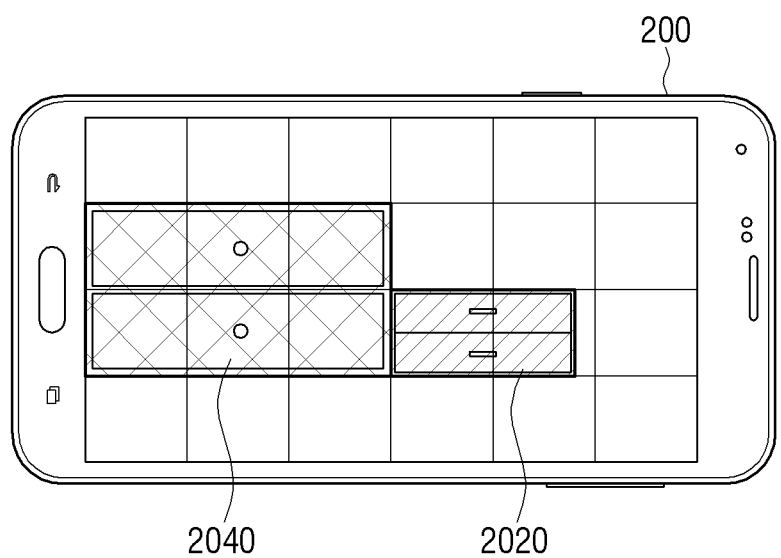

FIGS. 20A, 20B, and 20C are views to illustrate a method for grasping the size of a piece of furniture by using the remote image transmission system 1000, according to an exemplary embodiment.

In the embodiment of FIGS. 20A, 20B, and 20C, the display apparatus 200 should include the capturing unit 260 that includes the plurality of image pickup devices spaced apart from each other. By using a plurality of images generated by the capturing unit 260, the processor 230 may extract physical information of a space which is currently photographed. In addition, the processor 230 may extract physical information of a captured object from an image received from the image capturing apparatus 100. The processor 230 may match the size of the space currently photographed with the size of the received image to be equal to each other by using the extracted physical information.

Referring to FIG. 20A, the display apparatus 200 may receive an image 2010 regarding a first piece of furniture 2020 captured by the image capturing apparatus 100. The processor 230 may control to display a guide object in the form of a grid that provides size information with the received image 2010.

In addition, the processor 230 may control the display 220 to display a live view image 2030 regarding a space which is currently photographed by the capturing unit 260. The image 2030 of the space currently photographed includes a second piece of furniture 2040. The processor 230 may control the display 220 to display a guide object having a grid of the same length unit as the grid displayed on the received image 2010 (for example, one side of the square of the grid is equal to 10 cm) together with the live view image 2030.

In addition, the processor 230 may control the display 220 to display the received image 2010 with the live view image 2030 which is currently photographed. Referring to FIG. 20B, it can be known that the live view image 2030 and the received image 2010 are displayed. However, the live view image 2030 and the received image 2010 are not consistent with each other in their size ratios. This is because as illustrated in FIG. 20B, the sizes of the grids displayed on both images 2010 and 2030 are not consistent with each other.

As shown in FIG. 20C, the processor 230 may magnify or reduce the received image 2010 to make the grid sizes on the screens of the received image 2010 and the live view image 2030 consistent with each other.

By using the remote image transmission system 1000 according to an exemplary embodiment as described above, the user can intuitively compare the size of a first object included in an image received from the outside and the size of a second object which is photographed as a live view.

Figure 21:
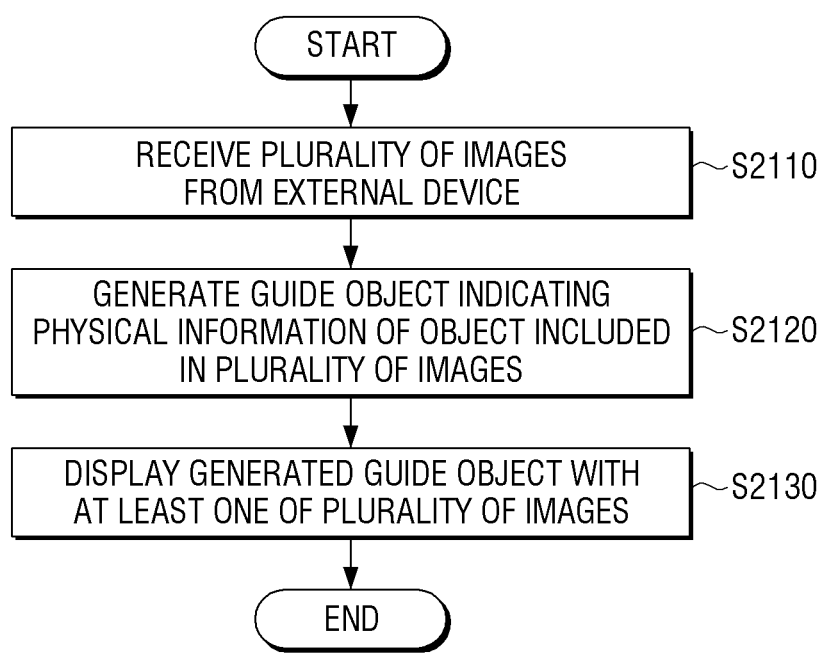
FIG. 21 is a flowchart to illustrate a method for displaying a guide of a display apparatus, according to an exemplary embodiment.

FIG. 21 is a flowchart to illustrate a method for displaying a guide of the display apparatus 200, according to an exemplary embodiment. In operation S2110, the display apparatus 200 may receive a plurality of images from an external device. The plurality of images should be images which are captured by the plurality of image pickup devices spaced from each other at the same time. For example, the plurality of images may be images which are captured by a smart phone that includes a dual camera. In addition, the display apparatus 200 may receive information on a distance between the plurality of image pickup devices and a focal distance of each image pickup device from the external device.

In addition, the display apparatus 200 may generate physical information of captured images based on the distance between the plurality of image pickup devices and the focal distance of the image pickup device. In operation S2120, by using the generated physical information, the display apparatus 200 may generate a guide object indicating physical information of an object included in the received images.

In addition, in operation S2130, the display apparatus 200 may display the generated guide object with at least one of the plurality of received images.

The method of displaying the guide of the display apparatus 200 according to various exemplary embodiments in addition to the guide displaying method shown in FIG. 21 has been described above with the description of the remote image transmission system 1000, and a description thereof is omitted.

Figure 22:
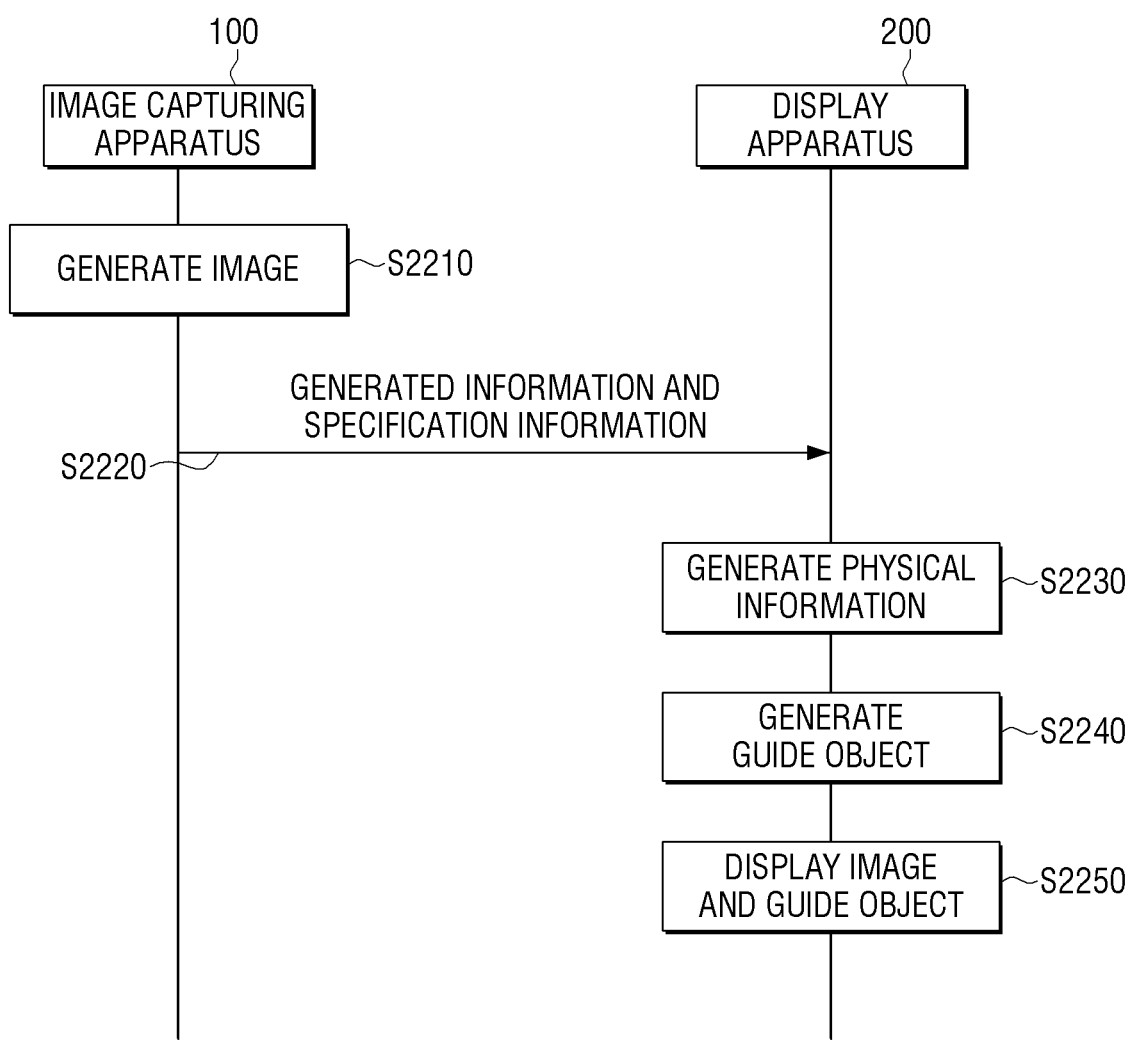
FIG. 22 is a sequence diagram to illustrate an operation of a remote image transmission system, according to an exemplary embodiment.

FIG. 22 is a sequence diagram to illustrate the operation of the remote image transmission system 1000, according to an exemplary embodiment. Referring to FIG. 22, the remote image transmission system 1000 may include the image capturing apparatus 100 and the display apparatus 200. In operation S2210, the image capturing apparatus 100 may generate a plurality of images captured by the plurality of image pickup devices which are spaced from each other. In addition, in operation S2220, the image capturing apparatus 100 may transmit the plurality of generated images and the specification information of the image capturing apparatus 100 to the display apparatus 200. For example, the specification information may be a distance between the plurality of image pickup devices and a focal distance of the image pickup device.

In operation S2230, by using the received specification information, the display apparatus 200 may generate physical information regarding a captured object. For example, the physical information may be information on the size or depth of the object. In operation S2240, the display apparatus 200 may generate a guide object for providing the generated physical information. In addition, in operation S2250, the display apparatus 200 may display the received images with the generated guide object.

According to another exemplary embodiment, the image capturing apparatus 100 may generate a guide object and transmit the generated guide object to the display apparatus 200 in conjunction with a captured image.

The above-described methods may be implemented in the form of program commands which can be implemented through various computer means, and may be recorded on a transitory or non-transitory computer readable medium. The computer readable medium may include program commands, data files, and data structures either alone or in combination. The program commands recorded on the medium may be those that are especially designed and configured for the present disclosure, or may be those that are publicly known and available to those skilled in the art. Examples of the computer-readable medium include magnetic recording media such as hard disks, floppy disks and magnetic tapes, optical recording media such as CD-ROMs and DVDs, magneto-optical recording media such as floptical disks, and hardware devices such as ROMs, RAMs and flash memories that are especially configured to store and execute program commands. Examples of the program commands include machine language codes created by a compiler, and high-level language codes that can be executed by a computer by using an interpreter. The hardware device may be configured to operate as one or more software modules to perform the operation of the present disclosure, and the reverse can be applied.

The foregoing exemplary embodiments and advantages are merely exemplary and are not to be construed as limiting the present inventive concept. The present teaching can be readily applied to other types of apparatuses. Also, the description of the exemplary embodiments is intended to be illustrative, and not to limit the scope of the claims, and many alternatives, modifications, and variations will be apparent to persons having ordinary skill in the art.

What is claimed is:

1. A remote image transmission system comprising:
a display apparatus; and
an image capturing apparatus comprising a plurality of cameras that are spaced from each other, the image capturing apparatus being configured to:
    capture a plurality of images, which include an object, at a same time by using the plurality of cameras, and
    transmit, to the display apparatus, the plurality of images and specification information indicating a distance between adjacent cameras from among the plurality of cameras and respective focal distances of the plurality of cameras, in conjunction with the plurality of captured images,
wherein the display apparatus is configured to:
    receive the plurality of images and the specification information from the image capturing apparatus,
    identify size information of the captured object based on the specification information,
    obtain a guide object indicating the size information of the captured object by using the plurality of received images and the specification information, and
    display the obtained guide object and at least one from among the plurality of images.

2. The remote image transmission system of claim 1, wherein the image capturing apparatus comprises:
a capturer comprising the plurality of cameras;
a communicator configured to communicate with the display apparatus; and
a processor configured to control the communicator to communicate with the display apparatus.

3. The remote image transmission system of claim 2, wherein the image capturing apparatus further comprises a light source configured to project light of an infrared wavelength, wherein at least one from among the plurality of cameras is configured to receive reflected light from the light of the infrared wavelength projected by the light source.

4. The remote image transmission system of claim 1, wherein the display apparatus comprises:

a communicator configured to communicate with the image capturing apparatus;

a display; and a processor configured to obtain the guide object indicating the size information of the captured object by using the plurality of received images and the specification information, and to control the display to display the obtained guide object and the at least one image from among the plurality of received images.

5. The remote image transmission system of claim 4, wherein the guide object is obtained in a form of at least one from among a ruler, a grid, and an arrow.

6. The remote image transmission system of claim 4, wherein the processor is further configured to detect an affected area within at least one image from among the plurality of received images, and to obtain a graphic object surrounding the detected affected area.

7. The remote image transmission system of claim 6, wherein the processor is further configured to perform filtering for changing an image characteristic of the detected affected area.

8. The remote image transmission system of claim 6, wherein the processor is further configured to control the display to display the graphic object surrounding the detected affected area, and to control the display to display a previously obtained graphic object which relates to a previously detected affected area within a previously received image.

9. The remote image transmission system of claim 8, wherein the processor is further configured to extract a characteristic point from the received at least one image within which the affected area has been detected, and to match a size of the graphic object surrounding the detected affected area with a size of the previously obtained graphic object based on the extracted characteristic point.

10. The remote image transmission system of claim 4, wherein the display apparatus further comprises an inputter configured to receive a selection of an object, and wherein the processor is further configured to obtain the guide object displaying the size information of the selected object.

11. The remote image transmission system of claim 4, wherein the processor is further configured to obtain a three-dimensional (3D) model of an object included in the plurality of images by using the plurality of received images.

12. The remote image transmission system of claim 4, wherein the display apparatus further comprises a capturer configured to obtain the plurality of images captured by the plurality of cameras that are spaced from each other, and wherein the display apparatus is further configured to extract physical information of an object captured by the image capturing apparatus by using the plurality of received images and the specification information, and to extract physical information of a captured space by using the plurality of captured images and the specification information, and to display at least one from among the plurality of received images and at least one from among the plurality of images captured by the display apparatus based on the extracted physical information.

13. A display apparatus comprising:

a communicator configured to communicate with an external device having a plurality of cameras that are spaced apart from each other and configured to capture a plurality of images which include an object;

a display; and a processor configured to:

receive, through the communicator, the plurality of images and specification information indicating a distance between adjacent cameras from among the plurality of cameras and respective focal distances of the plurality of cameras, in conjunction with the plurality of captured images, identify size information of the captured object included in the plurality of images based on the specification information, obtain a guide object indicating the size information of the captured object included in the plurality of images by using the plurality of received images and the specification information, and control the display to display the obtained guide object and at least one image from among the plurality of received images.

14. A method for displaying a guide of a display apparatus, the method comprising:

receiving, from an external device having a plurality of cameras that are spaced apart from each other and configured to capture a plurality of images which include an object, the plurality of images and specification information indicating a distance between adjacent cameras from among the plurality of cameras and respective focal distances of the plurality of cameras, in conjunction with the plurality of captured images;

identifying size information of the captured object included in the plurality of received images based on the specification information;

obtaining a guide object indicating the size information of the captured object included in the plurality of received images by using the plurality of received images and the specification information; and displaying the obtained guide object and at least one image from among the plurality of received images.

15. The method of claim 14, further comprising:

detecting an affected area within at least one image from among the plurality of received images;

obtaining a graphic object surrounding the detected affected area; and displaying the obtained graphic object.

16. The method of claim 15, further comprising matching and displaying a size of a graphic object which relates to a previously detected affected area within a previously received image with respect to a size of the graphic object surrounding the detected affected area within the at least one image from among the plurality of received images.

17. The method of claim 16, wherein the matching and displaying the size comprises:

extracting a characteristic point from the received at least one image within which the affected area has been detected; and matching the size of the graphic object surrounding the detected affected area with the size of the previously obtained graphic object based on the extracted characteristic point.

18. The method of claim 14, wherein the obtaining the guide object comprises:
   receiving a selection of an object included in at least one image from among the received plurality of images; and
   obtaining the guide object displaying the size information of the selected object.

\* \* \* \* \*